(12) United States Patent
Ra et al.

(10) Patent No.: US 9,433,645 B2
(45) Date of Patent: Sep. 6, 2016

(54) METHOD AND COMPOSITION FOR PREVENTING STEM CELL DISRUPTION AND AGGREGATION

(71) Applicants: R BIO CO., LTD., Seoul (KR); Jeong Chan Ra, Gyeonggi-do (KR)

(72) Inventors: Jeong Chan Ra, Gyeonggi-do (KR); Sung Keun Kang, Seoul (KR); Il Seob Shin, Seoul (KR)

(73) Assignees: Jeong Chan Ra, Gyeonggi-do (KR); R BIO CO., LTD., Seoul (KR)

( * ) Notice: Subject to any disclaimer, the term of this patent is extended or adjusted under 35 U.S.C. 154(b) by 0 days.

(21) Appl. No.: 14/394,402

(22) PCT Filed: Apr. 15, 2013

(86) PCT No.: PCT/KR2013/003141
§ 371 (c)(1),
(2) Date: Oct. 14, 2014

(87) PCT Pub. No.: WO2013/154404
PCT Pub. Date: Oct. 17, 2013

(65) Prior Publication Data
US 2015/0118194 A1     Apr. 30, 2015

(30) Foreign Application Priority Data

Apr. 13, 2012 (KR) .................. 10-2012-0038828

(51) Int. Cl.
| | |
|---|---|
| *C12N 5/074* | (2010.01) |
| *A61K 35/28* | (2015.01) |
| *C12N 5/0775* | (2010.01) |
| *A61K 31/616* | (2006.01) |

(52) U.S. Cl.
CPC ............. *A61K 35/28* (2013.01); *A61K 31/616* (2013.01); *C12N 5/0667* (2013.01); *C12N 2500/30* (2013.01); *C12N 2501/71* (2013.01); *C12N 2501/999* (2013.01)

(58) Field of Classification Search
CPC .................................................. C12N 5/0607
See application file for complete search history.

(56) References Cited

U.S. PATENT DOCUMENTS

| | | | |
|---|---|---|---|
| 7,429,488 B2 | 9/2008 | Fraser et al. | |
| 2010/0304477 A1* | 12/2010 | Buscher | C12N 5/0667 435/325 |

(Continued)

FOREIGN PATENT DOCUMENTS

| | | |
|---|---|---|
| KR | 10-2005-0109941 A | 11/2005 |
| KR | 10-0795708 B1 | 1/2008 |

(Continued)

OTHER PUBLICATIONS

Omori et al., "Optimization of a therapeutic protocol for intravenous injection of human mesenchymal stem cells after cerebral ischemia in adult rats", Brain Res., vol. 1236, pp. 30-38, (2008).

*Primary Examiner* — Rosanne Kosson
(74) *Attorney, Agent, or Firm* — Vorys, Sater, Seymour & Pease LLP; Mih Suhn Koh

(57) ABSTRACT

There is provided a method for preventing disruption and aggregation of stem cells. In addition, there is provided a stem cell composition for intravascular administration, in which stem cells are suspended in a solution containing aspirin. Further, there is provided a composition for preventing disruption or aggregation of stem cells, in which stem cells are suspended in a solution containing aspirin. According to the present invention, disruption and aggregation of cells may be prevented during transport or storage, such that the administered stem cells may stably reach the target tissue and exhibit the activity thereof in a more efficient manner, thereby remarkably increasing the effect of cell therapy using stem cells.

5 Claims, 2 Drawing Sheets

(56) References Cited

U.S. PATENT DOCUMENTS

2012/0020931 A1    1/2012  Yarmush et al.
2012/0122816 A1*  5/2012  Gjorstrup ............ A01N 1/0226
                                                            514/63

FOREIGN PATENT DOCUMENTS

| KR | 10-0818214 B1 | 3/2008 |
| KR | 10-2011-0038569 A | 4/2011 |
| WO | 2006/019357 A1 | 2/2006 |

* cited by examiner

METHOD AND COMPOSITION FOR PREVENTING STEM CELL DISRUPTION AND AGGREGATION

TECHNICAL FIELD

The present invention relates to a method for preventing disruption and aggregation of stem cells, and more particularly, to a method for preventing disruption and aggregation of stem cells capable of preventing cells from being disrupted or aggregated during transport or storage.

BACKGROUND ART

Stem cells refer to cells capable of differentiating into at least two types of cells while having self-replicating ability and may be classified into totipotent stem cells, pluripotent stem cells, and multipotent stem cell. Totipotent stem cells are cells having totipotent properties capable of developing into one perfect individual, and these properties are possessed by cells up to eight-cell stage after the fertilization of an oocyte and a sperm. When these cells are isolated and transplanted into the uterus, these cells may develop into one perfect individual. Pluripotent stem cells, which are cells capable of developing into various cells and tissue derived from the ectodermal, mesodermal and endodermal layers, are derived from an inner cell mass located inside of blastocysts generated after 4-5 days of fertilization. These cells are called "embryonic stem cells" and may differentiate into various other tissue cells but do not form new living organisms. Multipotent stem cells, which are stem cells capable of differentiating into only cells specific to tissue and organs containing these cells, are involved not only in the growth and development of various tissue and organs in the fetal, neonatal and adult periods but also in the maintenance of homeostasis of adult tissue and the function of inducing regeneration upon tissue damage. Tissue-specific multipotent cells are collectively called "adult stem cells".

The adult stem cells, which are obtained by harvesting cells already existing in various organs of human body to develop the cells into stem cells, are characterized by differentiating into only specific tissue. However, recently, experiments for differentiating adult stem cells into various tissue including liver cells, and the like, are successful, which is in the spotlight. Particularly, in regenerative therapy, which is therapy performed by actively utilizing cells for regeneration of biological tissue and organ having functional disorder or dissonance caused by a disease or accident and recovery of functions, a method including: collecting stem cells, blood-derived mononuclear cells, or bone marrow-derived mononuclear cells, inducing cell proliferation and/or differentiation by in vitro culture, and transducing selected undifferentiated (stem cells and/or precursor cells) and/or differentiated cells in a patient's body by implantation has been mainly used. As it is estimated that the existing method for treating a disease through classic medicine treatment methods or surgical methods will be replaced by cell/tissue replacement therapy for replacing damaged cells, tissue, or organs with healthful cells, tissue, or organs as described above, usages of the stem cells will be further increased.

Therefore, currently, various functions of the stem cells have been studied. Among them, cell therapy using mesenchymal stem cells has been spotlighted, and a technology of improving mesenchymal stem cells isolated from a human body so as to be suitable for treatment has been developed (WO 2006/019357, Korean Patent No. 0795708, and Korean Patent No. 0818214).

However, research into a method of preparing stem cells suitable for intracorporeal administration and having excellent safety has not been sufficiently conducted yet.

Therefore, the present inventors confirmed that in the case of suspending stem cells in a solution containing aspirin, disruption and aggregation of stem cells may be prevented, thereby completing the present invention.

DISCLOSURE—SUMMARY OF THE INVENTION

Technical Problem

An object of the present invention is to provide a method for preventing disruption and aggregation of stem cells.

Another object of the present invention is to provide a stem cell composition for intravascular administration.

Another object of the present invention is to provide a composition for preventing disruption or aggregation of stem cells.

Technical Solution

According to an aspect of the present invention, there is provided a method for preventing disruption and aggregation of stem cells including suspending stem cells in a solution containing aspirin.

According to another aspect of the present invention, there is provided a stem cell composition for intravascular administration, in which stem cells are suspended in a solution containing aspirin.

According to another aspect of the present invention, there is provided a composition for preventing disruption or aggregation of stem cells, in which stem cells are suspended in a solution containing aspirin.

DETAILED DESCRIPTION OF THE EMBODIMENTS

Figure 1:
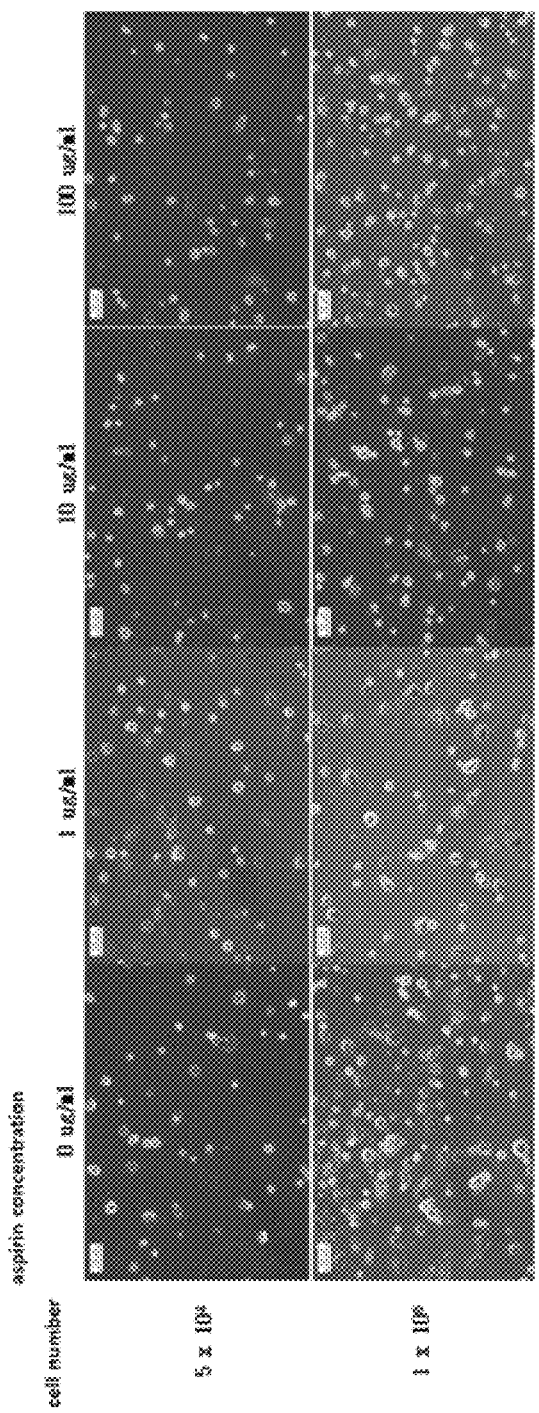
FIG. 1 is a photograph obtained by observing aggregation degrees of stem cells exposed to aspirin at various concentrations for 24 hours.

Unless otherwise defined herein, all of the technical and scientific terms used in the present specification have the same meanings as those understood by specialists in the skilled art to which the present invention pertains. Generally, nomenclature used in the present specification and experimental methods described below are well known and commonly used in the art.

As used herein, the term "stem cell" means a cell capable of differentiating into at least two types of cells while having self-replication ability, and the term "adult stem cell" means a stem cell generated at a stage at which a development process proceeds to thereby form each organ of an embryo or at an adult stage.

As used herein, the term "mesenchymal stem cell" means an undifferentiated stem cell isolated from a tissue of a human or mammals and may be derived from various tissues. Particularly, the mesenchymal stem cell may be a umbilical cord-derived mesenchymal stem cell, a umbilical cord blood-derived mesenchymal stem cell, a bone marrow-derived mesenchymal stem cell, an adipose-derived mesenchymal stem cell, a muscle-derived mesenchymal stem cell, a nerve-derived mesenchymal stem cell, a skin-derived mesenchymal stem cell, an amnion-derived mesenchymal stem cell, and a placenta-derived mesenchymal stem cell, and a technology of isolating the stem cell from each tissue has been known in the art.

As used herein, the term "adipose tissue-derived mesenchymal stem cell", which is an undifferentiated adult stem cell isolated from an adipose tissue, is briefly referred to as "adipose-derived adult stem cell", "adipose stem cell", or "adipose-derived stem cell" in the present specification. The adipose-derived mesenchymal stem cell may be obtained by a general method known in the art. An example of an isolation method thereof is as follows. That is, the adipose-derived mesenchymal stem cells may be isolated by a method of treating a stem cell layer attached to a culture vessel such as a flask, or the like, with trypsin after culturing a suspension containing adipose suspended in normal saline obtained by liposuction, and then recovering the treated stem cells, a method of directly recovering stem cells suspended in a small amount of normal saline by scraping using a scraper, or the like.

As used herein, the term "transport" means that stem cells itself, a vessel filled with a solution containing stem cells, or the like, are transported by means of transportation such as vehicle, or the like, and the term "storage" includes cold temperature storage as well as room temperature storage.

As used herein, the term "prevention of disruption and aggregation of stem cells" means that stem cells are maintained in a single cell form without being broken or aggregated. As an example, it means that stem cells being transported or stored are maintained in the single cell form without breakage of a cell membrane or aggregation between the cells.

Stem cells may be administered in a body by various methods, for example, an intravenous, intraarterial, or intraperitoneal administration method, or the like. Among them, since the intravenous administration method may simply and safely treat a disease without a surgical operation, the intravenous administration method is useful. However, in order to allow the intravenously administered stem cells to actually and stably reach a target site to obtain the desired treatment effect, various factors should be satisfied. First, the stem cells need to be intravascularly administered in a single cell form. The stem cells may be prepared in the single cell form by being treated with trypsin, or the like, for intracorporeal administration, but even in the case of the stem cells prepared in the single cell form, a cell membrane may be broken or aggregation between cells may be formed during transport or storage. In the case in which the aggregated stem cells rather than stem cells in the single form or broken cells are administered in the body by intravenous administration, or the like, the administered cells may be attached to vascular endothelial cells, blood platelets, or the like, to decrease a blood flow velocity or hinder blood circulation, and even cause occlusion of a micro-vessel, a blood vessel, or the like (D. Furlani et al., Microvasular Research 77 (2009) 370-376). Therefore, before the stem cells are intravascularly administered, it is essential that disruption or aggregation of cells is not generated, and after the stem cells are intravascularly administered, the stem cells should also stably reach a target site in a single cell form without disruption or aggregation of cells. Further, the stem cells should have a size suitable for intravascular administration so that the stem cells intravascularly administered do not decrease a blood flow velocity or form blood clotting. In addition, the stem cells should be administered at a predetermined concentration or more so that the stem cells reached the target site exhibit the desired treatment effect. Among the various factors as described above, the present invention is to provide stem cells suitable for intracorporeal administration and having excellent safety by preventing disruption and aggregation of the stem cells before intravascular administration.

The present invention provides a method for preventing disruption and aggregation of stem cells including suspending stem cells in a solution containing aspirin.

As used herein, the term "solution containing aspirin" means a solution containing an aspirin compound, and as a solvent, normal saline may be preferable. Besides, any solvent, for example, Hartman-D solution, phosphate buffered saline (PBS), or the like, may be used without limitations as long as it is generally used in the art. As the aspirin, an aspirin-like compound may be used as well as generally available aspirin products. In an Example of the present invention, the solution containing aspirin was prepared by adding acetylsalicylic acid (Sigma; A5376), Arthalgyl Injection, or aspirin lysine (Shinpoong) to normal saline. In this case, it is preferable that a content of the added aspirin is 0.0001 to 0.01 mg/ml. In the case in which the content of the added aspirin is more than the above-mentioned range, a survival rate of cells may be decreased, and in the case in which the content is less than the above-mentioned range, an effect of preventing disruption or aggregation of cells may be insignificant.

Since in the case of suspending stem cells in the solution containing aspirin, disruption and aggregation of stem cells are not generated during transport or storage, these stem cells may be directly applied to intracorporeal administration, such that these stem cells are useful. Therefore, preferably, the stem cells used at the time of intravascular administration may be used after being suspended in normal saline containing aspirin.

In another aspect, the present invention provides a stem cell composition for intravascular administration, in which stem cells are suspended in a solution containing aspirin.

In another aspect, the present invention provides a composition for preventing disruption or aggregation of stem cells, in which stem cells are suspended in a solution containing aspirin.

As the stem cells used in the present invention, preferably, adult stem cells may be used. Among them, adult stem cells obtained from adipose tissue or epithelial tissue such as hair follicle, amnion, or the like, may be used. Most preferably, adipose tissue-derived adult stem cells may be used. Mesenchymal stem cells (MSCs) may be used, and particularly, adipose tissue-derived mesenchymal stem cells (AdMSCs) may be used.

Preferably, the adipose or epithelial tissue is derived from a mammal, and more preferably, the adipose or epithelial tissue is derived from a human. In the Example of the present invention, human adipose tissue-derived mesenchymal stem cells (hAdMSCs) were used.

As a medium used to obtain the stem cells, a general medium known in the art as a medium suitable for culturing stem cells may be used. For example, there are minimal essential medium (MEM), Dulbecco modified Eagle medium (DMEM), Roswell Park Memorial Institute medium (RPMI), and Keratinocyte serum free medium (K-SFM). In addition, a medium used in the art may be used.

Preferably, a medium selected from a group consisting of M199/F12 (mixture)(GIBCO), MEM-alpha medium (GIBCO), DMEM medium with low glucose (Welgene), MCDB 131 medium (Welgene), IMEM medium (GIBCO), and K-SFM may be used. Particularly, among them, K-SFM medium may be preferably used.

The medium used to obtain the stem cells may be supplemented with additives known in the art, the additive suppressing differentiation of the stem cells while promoting proliferation of an undifferentiated phenotype of the stem cells. In addition, the medium may contain a neutral buffer (for example, phosphate and/or high concentration bicarbonate) in an isotonic solution and protein nutrients (for example, serum such as fetal bovine serum (FBS), serum replacements, albumin, or essential or non-essential amino acids such as glutamine). Further, the medium may contain lipids (fatty acids, cholesterol, an HDL or LDL extract of serum) and other components found in most preservation media of this kind (such as insulin or transferrin, nucleosides or nucleotides, pyruvate, a sugar source such as glucose, selenium in any ionized form or salt, a glucocorticoid such as hydrocortisone and/or a reducing agent such as β-mercaptoethanol).

In addition, it is beneficial that the medium contains anti-clumping agents, for example, the ones sold by Invitrogen (Cat #0010057AE) in order to prevent cells from adhering to each other, adhering to a vessel wall, or forming excessively large clusters.

Among them, it is advantageous to use one or more of the following additional additive:
  Stem cell factor (SCF, Steel factor), other ligands or antibodies that dimerize c-kit, and other activators of the same signal transduction pathway;
  Ligands for other tyrosine kinase related receptors, such as the receptors for platelet-derived growth factor (PDGF), macrophage colony-stimulating factor, Flt-3 ligand, and vascular endothelial growth factor (VEGF);
  Factors increasing cyclic AMP levels, such as forskolin;
  Factors inducing gp130, such as LIE or Oncostatin-M;
  Hematopoietic growth factors, such as thrombopoietin (TPO);
  Transforming growth factors such as TGFβ1; and
  Neurotrophines, such as CNTF.

Particularly, a medium used to culture adipose stem cells in an exemplary embodiment of the present invention preferably contains NAC, calcium, insulin, hydrocortisone, and an antioxidant. More preferably, a medium containing two or more components of FBS, NAC, calcium, rEGF, insulin, hydrocortisone, and the antioxidant may be used. As the antioxidant, an antioxidant selected from selenium, ascorbic acid, vitamin E, catechin, lycopene, beta-carotene, coenzyme Q-10, eicosapentaenoic acid (EPA), docosahexanoic acid (DHA), and the like, may be used. Among them, selenium may be preferably used. In the Example of the present invention, selenium was used as the antioxidant, and a preferable amount of the used selenium was 0.5 to 10 ng/ml.

In Example of the present invention, adipose-derived mesenchymal stem cells were cultured in the medium having the above-mentioned composition. The adipose-derived mesenchymal stem cells may be obtained by the following method. First, human adipose tissue obtained from the abdomen by liposuction, or the like, was isolated and washed with PBS. Then, the isolated tissue was cut finely, digested using a DMEM medium supplemented with collagenase, washed with PBS, and then centrifuged at 1000 rpm for 5 minutes. A supernatant was removed and pellets remaining at a bottom were washed with PBS, followed by centrifugation at 1000 rpm for 5 minutes. Floating materials were removed using a 100-mesh, and the resulting cells were washed again with PBS. The resulting cells were cultured in a DMEM (10% FBS, 2 mM NAC, 0.2 mM ascorbic acid) medium, and after overnight, cells that were not adhered to a bottom of a culture vessel were washed with PBS. Then, the remaining cells were cultured while the medium was replaced with K-SFM medium containing NAC, ascorbic acid, calcium, rEGF, insulin, and hydrocortisone every other day, such that mesenchymal stem cells were isolated and sub-cultured, thereby making it possible to obtain the mesenchymal stem cells. However, the mesenchymal stem cells may be obtained by a method known in the art as well as the above-mentioned method.

In the case of treating the stem cells cultured in the medium having the above-mentioned composition with trypsin, stem cells in a single cell form may be obtained. In this case, trypsin is treated in order to suppress aggregation of cells to thereby allow the cells to have a single cell form, and any material may be used instead of trypsin as long as the material may suppress aggregation of the cells.

Hereinafter, the present invention will be described in detail through the Examples. However, these Examples are only to illustrate the present invention, and those skilled in the art will appreciate that these Examples are not to be construed as limiting a scope of the present invention.

EXAMPLE

Example 1

Isolation of Human Adipose Tissue-Derived Mesenchymal Stem cell

Adipose tissue was isolated from abdominal fat by liposuction and washed with PBS. The isolated adipose tissue was cut finely and then digested in DMEM media supplemented with collagenase type 1 (1 mg/ml) at 37° for 2 hours. After washing the collagenase treated tissue with PBS, the digested tissue was centrifuged at 1000 rpm for 5 minutes to remove a supernatant, and pellets were washed with PBS and then centrifuged at 1000 rpm for 5 minutes. After removing floating materials by filtering using a 100-mesh, the resulting cells were washed with PBS and cultured in a DMEM supplemented with 10% FBS, 2 mM N-acetyl-L-cysteine (NAC) and 0.2 mM ascorbic acid.

After overnight, non-adherent cells were washed with PBS. Then, the remaining cells were sub-cultured while the medium was replaced with Keratinocyte-SFM media (K-SFM) containing 5% FBS, 2 mM NAC, 0.2 mM ascorbic acid, 0.09 mM calcium, 5 ng/ml rEGF, 5 ng/ml insulin, 10 ng of bFGF, 74 ng/ml hydrocortisone, and 1 ng/ml selenium every other day, thereby isolating adipose-derived mesenchymal stem cells.

Example 2

Isolation of Human Adipose Tissue-Derived Mesenchymal Stem cell 2-1: Single Cell Maintenance Ability of Stem Cells
(1) Treatment with Normal Saline containing Acetylsalicylic Acid at Each Concentration
After the adipose tissue-derived mesenchymal stem cells isolated in Example 1 were treated with trypsin, the trypsin treated adipose tissue-derived mesenchymal stem cells (1.0×

$10^7$ cells) were suspended in normal saline containing acetylsalicylic acid (Sigma; A5376) at each concentration, and survival rates at 12 and 24 hours were observed. The normal saline containing acetylsalicylic acid was prepared by adding acetylsalicylic acid to normal saline at each concentration and performing sonication at 37□ for 30 minutes.

TABLE 1

| Suvival rate | Aspirin concentration (mg/10 ml) | | | |
|---|---|---|---|---|
| | 0 | 1 | 2 | 5 |
| 12 hours | 85% | 50% | 20% | 10% |
| 24 hours | 70% | 10% | 10% | 5% |

As an experimental result, it may be confirmed that in the case in which an amount of aspirin added to 10 ml of normal saline was 1.0 mg or more, a cytotoxic effect was exhibited.

(2) Treatment with Normal Saline Containing Arthalgyl Injection at Each Concentration After the adipose tissue-derived mesenchymal stem cells isolated in Example 1 were treated with trypsin, the trypsin treated adipose tissue-derived mesenchymal stem cells ($1.0 \times 10^7$ cells) were suspended in normal saline containing Arthalgyl Injection at each concentration, and survival rates at 12, 24, 48, and 72 hours were observed.

TABLE 2

| Suvival rate | Aspirin concentration (mg/10 ml) | | | |
|---|---|---|---|---|
| | 0 | 0.001 | 0.01 | 0.1 |
| 12 hours | 95% | 91% | 90% | 90% |
| 24 hours | 90% | 87% | 85% | 84% |
| 48 hours | 85% | 80% | 77% | 74% |
| 72 hours | 65% | 63% | 61% | 61% |

As an experimental result, it may be confirmed that in the case in which an amount of aspirin added to 10 ml of normal saline was 0.001 to 0.1 mg, aspirin did not affect survival of the adipose stem cells. At the time of suspending the adipose stem cells in the solution containing aspirin, the suspended adipose stem cells may be stored up to 72 hours, but it is preferable that the suspended adipose stem cells are treated within 24 hours.

(3) Proliferation Ability of Stem Cells Treated with Normal Saline Containing Arthalgyl Injection at Each Concentration After the adipose tissue-derived mesenchymal stem cells isolated in Example 1 were treated with trypsin, the trypsin treated adipose tissue-derived mesenchymal stem cells ($1.0 \times 10^7$ cells) were suspended in normal saline containing Arthalgyl Injection at each concentration, and survival rates after 24 hours were observed.

TABLE 3

| Survival rate | Aspirin concentration (mg/10 ml) | | | |
|---|---|---|---|---|
| | 0 | 0.001 | 0.01 | 0.1 |
| 24 hours | 95% | 92% | 91% | 91% |

As an experimental result, it may be confirmed that in the case in which an amount of aspirin added to 10 ml of normal saline was 0.001 to 0.1 mg, aspirin did not affect proliferation ability of the adipose stem cells.

In addition, as a result obtained by observing the number of cells and a survival rate after culturing the suspended cells ($1.0 \times 10^6$ cells) for 7 days, as shown in Table 4, the survival rate was 86 to 90%, and as shown in Table 5, the number of cells was not almost changed by the addition of aspirin (0.001~0.1 mg/10 ml).

TABLE 4

<Survival Rate after 24 hours at Each Concentration of Aspirin (n = 3)>

| Survival rate | Aspirin concentration (mg/10 ml) | | | |
|---|---|---|---|---|
| | 0 | 0.001 | 0.01 | 0.1 |
| LM091936 P3 | 90% | 90% | 85% | 87% |
| LM091951 P3 | 91% | 90% | 89% | 86% |
| LM091954 P3 | 92% | 90% | 90% | 88% |
| average | 91 ± 1% | 90 ± 0% | 88 ± 2.6% | 87 ± 1% |

TABLE 5

<At the Time of Suspending Cells for 24 Hours at Each Concentration of Aspirin and Culturing, Influence of Proliferation Ability (n = 3)>

| Number of cells | Aspirin concentration (mg/10 ml) | | | |
|---|---|---|---|---|
| | 0 | 0.001 | 0.01 | 0.1 |
| LM091936 P3 | $8.0 \times 10^3$ | $7.6 \times 10^3$ | $8.2 \times 10^3$ | $7.8 \times 10^3$ |
| LM091951 P3 | $1.18 \times 10^7$ | $1.32 \times 10^7$ | $1.1 \times 10^7$ | $1.12 \times 10^7$ |
| LM091954 P3 | $1.02 \times 10^7$ | $1.0 \times 10^7$ | $1.3 \times 10^7$ | $1.02 \times 10^7$ |

(4) Aggregation of Stem Cells Treated with Normal Saline Containing Arthalgyl Injection at Each Concentration After treating the adipose-derived mesenchymal stem cells isolated in Example 1 with trypsin and suspending the trypsin treated adipose-derived mesenchymal stem cells in normal saline containing Arthalgyl Injection at each concentration, aggregation degrees after 24 and 72 hours were observed.

As a result, it may be confirmed that after 24 hours, in a control group, aggregation was most frequently observed, and it may be appreciated that in the case in which an amount of the added Arthalgyl Injection is 0.001 to 0.1 mg, aggregation of the adipose stem cells was decreased (FIG. 1). In a high concentration ($1 \times 10^5$ cells) stem cell experimental group as well as a low concentration ($5 \times 10^4$ cells) stem cell experimental group, an aggregation prevention effect of aspirin was confirmed.

Figure 2:
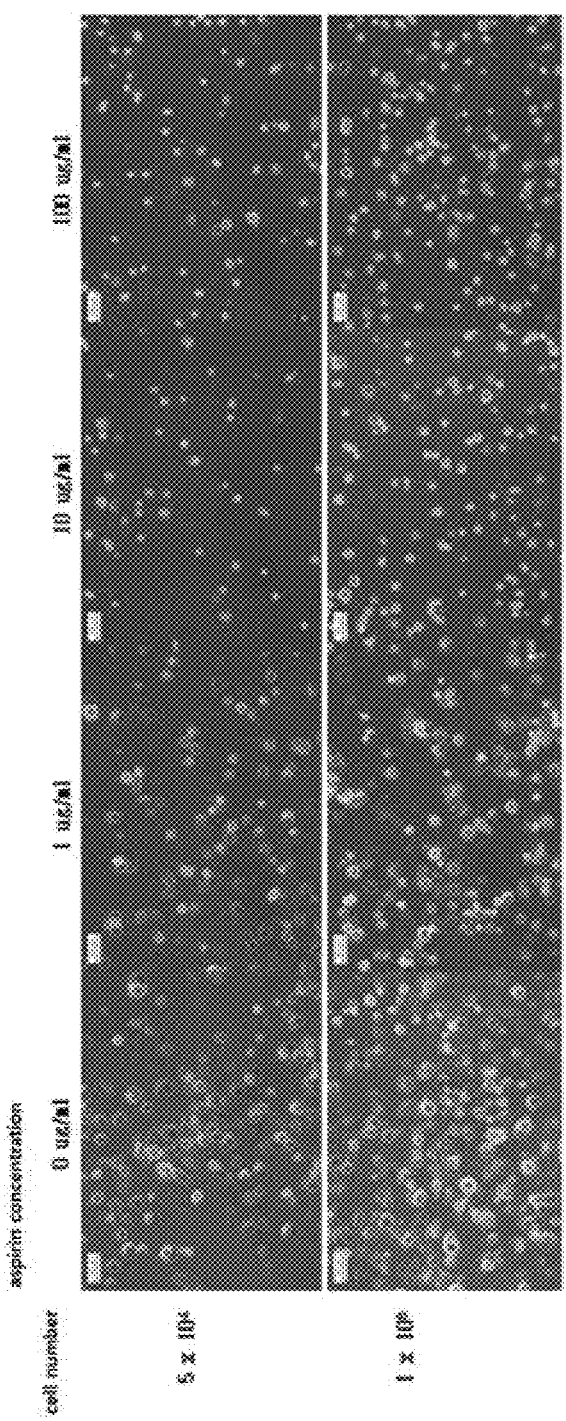
FIG. 2 is a photograph obtained by observing aggregation degrees of stem cells exposed to aspirin at various concentrations for 72 hours.

As a result obtained by confirming aggregation degrees after 72 hours, in a control group and a group treated with 1 μg/ml aspirin, apoptosis of cells together with an aggregation phenomenon was observed, but in groups treated with at least 10 μg/ml aspirin, this phenomenon was not observed as shown in FIG. 2.

(5) Characteristics of Stem Cells Treated with Normal Saline Containing Aspirin Lysine (Shinpoong)

After the adipose tissue-derived mesenchymal stem cells isolated in Example 1 were treated with trypsin, the trypsin treated adipose tissue-derived mesenchymal stem cells ($1.0 \times 10^6$ cells) were suspended in normal saline containing aspirin lysine (Shinpoong) at each concentration and cultured for 5 days, and the number of cells was measured. Then, after cold-temperature storage for 24 hours, FACS was measured, thereby confirming characteristics of the cells.

TABLE 6

| Expression rate | Aspirin concentration (mg/10 ml) | |
|---|---|---|
| | 0 | 0.1 |
| CD29 | 99.97% | 99.97% |
| CD31 | 0% | 0.21% |
| CD44 | 99.45% | 99.25% |
| CD45 | 0.19% | 0.17% |

As an experimental result, a cell survival rate depending on the concentration of aspirin lysine was slightly decreased, but the decrease was not significant. In addition, there was an individual difference, but there was also almost no change in the number of cells after culturing for 5 days. In the case of characteristics of the adipose-derived mesenchymal stem cells stored at a cold temperature for 24 hours after being suspended in normal saline containing aspirin for 24 hours, it was observed that there is no influence of the concentration of aspirin.

As an experimental result, the cytotoxic effect of aspirin lysine to the survival rate was not shown, and it was observed that in the case of storing the adipose-derived mesenchymal stem cells in normal saline containing aspirin, aggregation may be prevented without causing changes in the characteristics of cells.

INDUSTRIAL APPLICABILITY

According to the present invention, disruption and aggregation of stem cells during transport and storage may be prevented, such that stem cells suitable for intracorporeal administration and having excellent safety may be obtained, thereby remarkably increasing an effect of cell therapy by administration of the stem cells.

Although the present invention has been described in detail based on particular features thereof, it is obvious to those skilled in the art that these specific technologies are merely preferable embodiments and thus the scope of the present invention is not limited to the embodiments. Therefore, the substantial scope of the present invention is defined by the accompanying claims and equivalent thereof.

The invention claimed is:

1. A method for inhibiting disruption and aggregation of stem cells, the method comprising: suspending stem cells in a solution containing aspirin in an amount effective to inhibit said disruption and aggregation.

2. The method of claim 1, wherein said solution containing aspirin further comprises normal saline, Hartman-D solution or phosphate buffered saline (PBS).

3. The method of claim 1, wherein the aspirin is an amount of 0.0001 to 0.01 mg/ml.

4. The method of claim 1, wherein said stem cells are adult stem cells.

5. The method of claim 4, wherein said stem cells are adipose tissue-derived mesenchymal stem cells (AdMSCs).

* * * * *